United States Patent
Kim

(10) Patent No.: US 10,165,978 B2
(45) Date of Patent: Jan. 1, 2019

(54) METHOD FOR MEASURING HUMAN BODY INFORMATION, AND ELECTRONIC DEVICE THEREOF

(71) Applicant: Samsung Electronics Co., Ltd., Gyeonggi-do (KR)

(72) Inventor: Yong-Yi Kim, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 178 days.

(21) Appl. No.: 15/133,975

(22) Filed: Apr. 20, 2016

(65) Prior Publication Data

US 2016/0310071 A1 Oct. 27, 2016

(30) Foreign Application Priority Data

Apr. 24, 2015 (KR) .................. 10-2015-0058339

(51) Int. Cl.
    *A61B 5/00* (2006.01)
    *A61B 5/11* (2006.01)
    *A61B 5/04* (2006.01)

(52) U.S. Cl.
    CPC .......... *A61B 5/4872* (2013.01); *A61B 5/0002* (2013.01); *A61B 5/0077* (2013.01); *A61B 5/1116* (2013.01); *A61B 5/6898* (2013.01); *A61B 5/743* (2013.01); *A61B 5/04012* (2013.01); *A61B 5/4875* (2013.01); *A61B 2503/12* (2013.01); *A61B 2562/0219* (2013.01); *A61B 2562/0271* (2013.01)

(58) Field of Classification Search
    CPC ............................................. A61B 2562/0219
    USPC ............................................................ 348/77
    See application file for complete search history.

(56) References Cited

U.S. PATENT DOCUMENTS

| | | | | |
|---|---|---|---|---|
| 8,213,679 | B2* | 7/2012 | Yao | G06K 9/00785 348/169 |
| 9,788,759 | B2* | 10/2017 | Ferrantelli | A61B 5/1079 |
| 2004/0181141 | A1* | 9/2004 | Kislov | A61B 5/02116 600/393 |
| 2010/0021009 | A1* | 1/2010 | Yao | G06K 9/00785 382/103 |
| 2011/0043206 | A1* | 2/2011 | Kimura | G01R 33/56341 324/309 |
| 2011/0166491 | A1* | 7/2011 | Sankai | A41D 13/1281 601/84 |
| 2012/0086793 | A1* | 4/2012 | Anabuki | H04N 7/144 348/77 |
| 2012/0281878 | A1* | 11/2012 | Matsuda | G06T 7/0046 382/103 |
| 2015/0223730 | A1* | 8/2015 | Ferrantelli | A61B 5/1072 600/476 |

(Continued)

FOREIGN PATENT DOCUMENTS

KR 1020100012402 2/2010

*Primary Examiner* — Paulos M Natnael
(74) *Attorney, Agent, or Firm* — The Farrell Law Firm, P.C.

(57) ABSTRACT

A method of measuring human body information and an electronic device thereof are provided. The method includes displaying a guide image when a human body measurement mode is detected, acquiring, by a camera, a human body image, displaying the human body image, measuring a human body when the human body image corresponds to the guide image and outputting a result of the measurement of the human body.

16 Claims, 19 Drawing Sheets

(56) References Cited

U.S. PATENT DOCUMENTS

2016/0174846 A9* 6/2016 Ferrantelli .......... A61B 5/0077
                                                600/476
2016/0228011 A1* 8/2016 Tsubaki ............... A61B 5/0077
2016/0310071 A1* 10/2016 Kim ..................... A61B 5/4872
2017/0086791 A1* 3/2017 Chae .................... A61B 8/469

* cited by examiner

METHOD FOR MEASURING HUMAN BODY INFORMATION, AND ELECTRONIC DEVICE THEREOF

PRIORITY

This application claims priority under 35 U.S.C. § 119(a) to Korean Patent Application Serial No. 10-2015-0058339, which was filed on Apr. 24, 2015, the entire content of which is incorporated herein by reference.

BACKGROUND

1. Field of the Disclosure

The present disclosure generally relates to a method and apparatus for measuring information, and more particularly, to a method for measuring human body information and an electronic device thereof.

2. Description of the Related Art

The term "human body" may refer to the entire body of a human being or refer to a physical structure that an organism has. The term "health" may refer to a physical, mental, or social state. In addition, detailed elements of health may be classified into physical elements (physical measurement values such as height or weight, various internal organs, etc.), functional elements (physiological functions of various organs, overall physical strength, etc.) and mental elements. Measuring health information of a human body is very important in preventing and managing diseases. Hospitals are currently provided with various devices for measuring health information and diagnosing diseases. In addition, individuals have electronic devices for measuring human body information, such as a manometer, a blood glucose meter, etc., in their respective households to measure their own health information and manage their health.

An electronic device may have a health care sensor mounted therein to measure health information that an individual manages. That is, the health care function of the electronic device may enhance managing individual health and preventing diseases, rather than curing diseases. When a measuring device measures health using a health care sensor, the device may require instructions that users should pay attention to for exact measurements. In particular, the device has a limit in that the device has to follow the directions of medical personnel in relation to a measurement posture of a person to be measured.

SUMMARY

An aspect of the present disclosure is to address at least the above-mentioned problems and/or disadvantages and to provide at least the advantages described below. Accordingly, an aspect of the present disclosure provides a method for measuring human body information, and an electronic device thereof.

Another aspect of the present disclosure provides a method for guiding a measurement posture of a user (a person to be measured) during measurement, and measuring health when the measurement posture is detected, and an electronic device thereof.

Another aspect of the present disclosure provides a method for photographing a measurement posture of a user (a person to be measured) using a camera when measuring a user's body fat, guiding the measurement posture, and measuring human body information when the measurement posture is detected, and an electronic device thereof.

Another aspect of the present disclosure provides a method for photographing a measurement posture of a user (a person to be measured) using a camera when measuring a user's body fat, guiding the measurement posture, and acquiring an image of the person to be measured during photographing and forming a database by storing the measured human body information and the image, and an electronic device thereof.

According to an aspect of the present disclosure, a method of operating an electronic device includes displaying a guide image when a human body measurement mode is detected, acquiring, by a camera, a human body image, displaying the human body image, measuring a human body when the human body image corresponds to the guide image and outputting a result of the measurement of the human body.

According to another aspect of the present disclosure, an electronic device includes a human body sensor configured to detect human body information, a camera configured to photograph a human body image, a display configured to display a guide image and the human body image and a processor configured to, when the human body image corresponds to the guide image, measure a human body, and output a result of the measurement of the human body.

According to another aspect of the present disclosure, a computer readable recording medium includes a program for executing the operations of, when a human body measurement mode is detected, displaying a guide image, acquiring, by a camera, a human body image, displaying a human body image, measuring a human body when the human body image corresponds to the guide image and outputting a result of the measurement of the human body.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION

Figure 1:
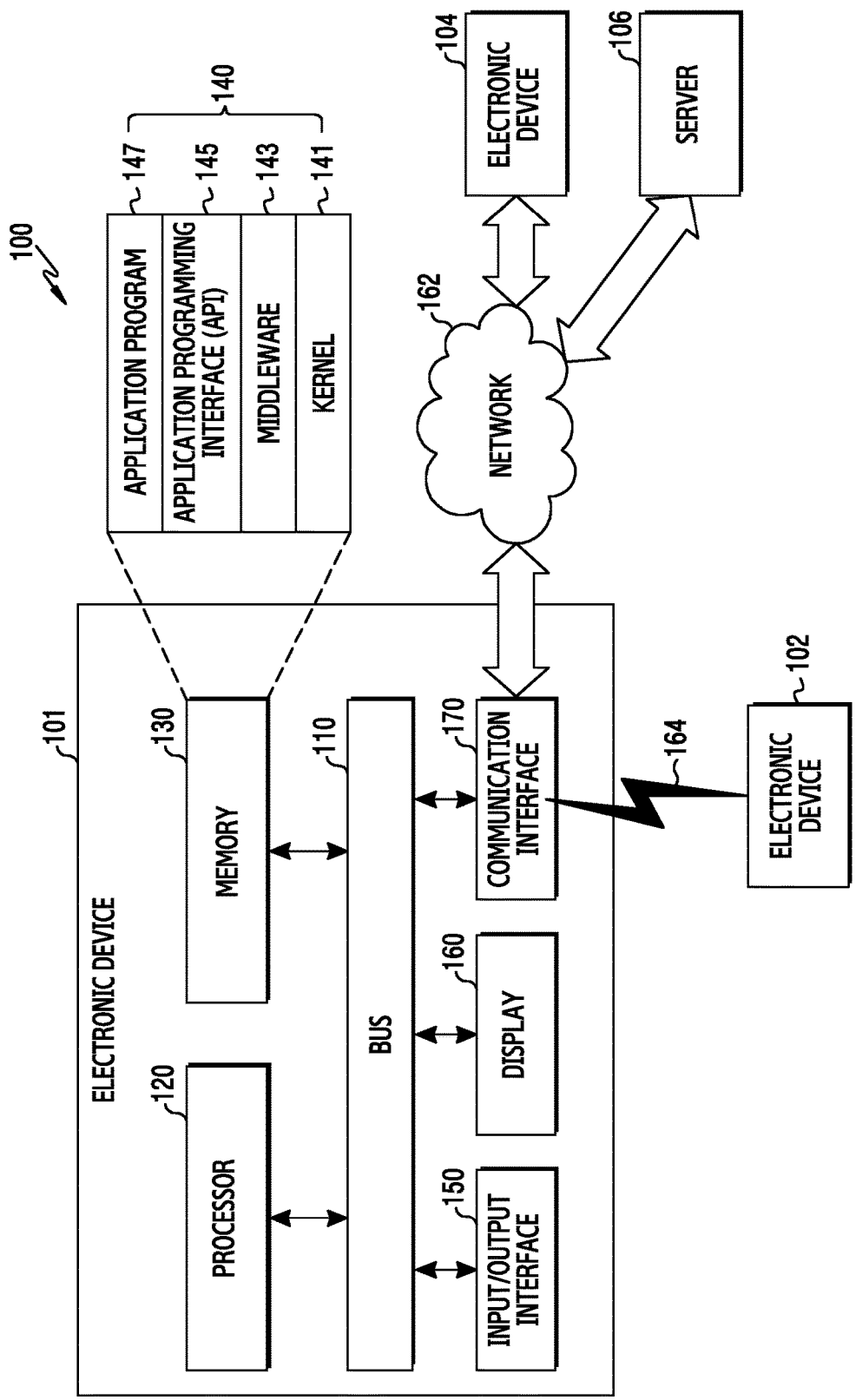
FIG. 1 illustrates a block diagram of a network environment including an electronic device according to various embodiments of the present disclosure.

Hereinafter, various embodiments of the present disclosure will be described in detail with reference to the accompanying drawings. However, it should be understood that there is no limiting the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expressions "have", "may have", "include", or "may include" refer to the existence of a corresponding feature (e.g., numeral, function, operation, or constituent element such as component), and do not exclude one or more additional features.

The expressions "A or B", "at least one of A or/and B", or "one or more of A or/and B" may include all possible combinations of the items listed. For example, the expressions "A or B", "at least one of A and B", or "at least one of A or B" refer to all of (1) including at least one A, (2) including at least one B, or (3) including both at least one A and at least one B.

The expressions "a first", "a second", "the first", or "the second" used in various embodiments of the present disclosure may modify various components regardless of the order and/or the importance but does not limit the corresponding components. For example, a first user device and a second user device indicate different user devices although both are user devices. For example, a first element may be referred to as a second element, and similarly, a second element may be referred to as a first element without departing from the scope of the present disclosure.

It will be understood that when an element (e.g., first element) is referred to as being (operatively or communicatively) "connected," or "coupled," to another element (e.g., second element), it may be directly connected or directly coupled to the other element or any other element (e.g., third element) may be interposed between them. In contrast, it will be understood that when an element (e.g., first element) is referred to as being "directly connected," or "directly coupled" to another element (second element), there are no elements (e.g., third element) interposed between them.

The expression "configured to" may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) dedicated to performing the corresponding operations or a general-purpose processor (e.g., central processing unit (CPU) or application processor (AP)) that may perform the corresponding operations by executing one or more software programs stored in a memory device.

The terms and expressions used herein are merely for the purpose of describing particular embodiments and do not limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Terms such as those defined in a generally used dictionary may be interpreted to have the same meanings as the contextual meanings in the relevant field of art, and are not to be interpreted to have ideal or excessively formal meanings unless clearly defined in the present disclosure. In some cases, even the terms defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments of the present disclosure, the wearable device may include at least one of an accessory type (e.g., a watch, a ring, a bracelet, an anklet, a necklace, eyeglasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

According to various embodiments of the present disclosure, the electronic device may be a home appliance. The home appliance may include at least one of, for example, a television, a Digital Video Disk (DVD) player, an audio player, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment of the present disclosure, the electronic device may include at least one of various medical devices (e.g., various portable medical measuring devices (a blood glucose monitoring device, a heart rate monitoring device, a blood pressure measuring device, a body temperature measuring device, a body fat measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Device, an electronic device for a ship (e.g., a navigation device for a ship, and a gyro-compass), avionics, security devices, an automotive head unit, a robot for home or industry, an automatic teller machine (ATM) in banks, point of sale (POS) terminal in a shop, or Internet of things device (e.g., a light bulb, various sensors, electric or gas meter, a sprinkler device, a fire alarm, a thermostat, a streetlamp, a toaster, a sporting good, a hot water tank, a heater, a boiler, etc.).

According to various embodiments of the present disclosure, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device may be a combination of one or more of the aforementioned various devices. The electronic device may be a flexible device. Further, the electronic device is not limited to the aforementioned devices, and may include a new electronic device according to the development of new technologies.

Hereinafter, an electronic device according to various embodiments of the present disclosure will be described with reference to the accompanying drawings. As used herein, the term "user" may indicate a person who uses an electronic device or a device (e.g., an artificial intelligence electronic device) that uses an electronic device. FIG. 1 illustrates a block diagram of a network environment including an electronic device according to various embodiments of the present disclosure.

Referring to FIG. 1, the electronic device 101 in the network environment 100 will be described. The electronic device 101 includes a bus 110, a processor 120, a memory 130, an input/output interface 150, a display 160, and a communication interface 170. According to an embodiment of the present disclosure, the electronic device 101 may omit at least one of the above elements or may further include other elements. The bus 110 may include, for example, a circuit for connecting the elements 110-170 and transferring control messages and/or data between the elements.

The processor 120 may include one or more of a Central Processing Unit (CPU), an Application Processor (AP), and a Communication Processor (CP). The processor 120, may carry out operations or data processing relating to control and/or communication of at least one other element of the electronic device 101.

The memory 130 may include a volatile memory and/or a non-volatile memory. The memory 130 may store, for example, instructions or data relevant to at least one other element of the electronic device 101. The memory 130 stores software and/or a program 140. The program 140 includes a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or function implemented by the other programs (e.g., the middleware 143, the API 145, or the application programs 147). Furthermore, the kernel 141 may provide an interface through which the middleware 143, the API 145, or the application programs 147 may access the individual elements of the electronic device 101 to control or manage the system resources.

The middleware 143, for example, may function as an intermediary for allowing the API 145 or the application programs 147 to communicate with the kernel 141 to exchange data.

In addition, the middleware 143 may process one or more task requests received from the application programs 147 according to set priorities. For example, the middleware 143 may set priorities for using the system resources (e.g., the bus 110, the processor 120, the memory 130, or the like) of the electronic device 101, to at least one of the application programs 147. For example, the middleware 143 may perform scheduling or load balancing on the one or more task requests by processing the one or more task requests according to the set priorities.

The API 145 is an interface through which the application programs 147 control functions provided from the kernel 141 or the middleware 143, and may include, for example, at least one interface or function (e.g., instruction) for file control, window control, image processing, or text control.

The input/output interface 150, for example, may function as an interface that transfers instructions or data input from a user or another external device to the other element(s) of the electronic device 101. Furthermore, the input/output interface 150 may output the instructions or data received from the other element(s) of the electronic device 101 to the user or another external device.

The display 160 may include, for example, a Liquid Crystal Display (LCD), a Light Emitting Diode (LED) display, an Organic Light Emitting Diode (OLED) display, a Micro Electro Mechanical System (MEMS) display, or an electronic paper display. The display 160, may display various types of content (e.g., text, images, videos, icons, or symbols) for the user. The display 160 may include a touch screen and may receive a touch, gesture, proximity, or hovering input using an electronic pen or a user's body part.

The communication interface 170, for example, may control communication between the electronic device 101 and an external device (e.g., the first external electronic device 102, the second external electronic device 104, or a server 106). For example, the communication interface 170 may be connected to a network 162 through wireless or wired communication to communicate with the external device 104 or the server 106.

The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), WiBro (Wireless Broadband), and Global System for Mobile Communications (GSM), as a cellular communication protocol. In addition, the wireless communication may include, for example, short range communication 164. The short-range communication 164 may be performed by using at least one of, for example, Wi-Fi, Bluetooth, Near Field Communication (NFC), and Global Navigation Satellite System (GNSS). The GNSS may include at least one of, for example, a Global Positioning System (GPS), a Global Navigation Satellite System (Glonass), a Beidou Navigation Satellite System (Beidou), and a European Global Satellite-based Navigation System (Galileo), according to a use area, a bandwidth requirement, and the like. Hereinafter, in the present disclosure, the term "GPS" may be interchangeably used with the term "GNSS". The wired communication may include at least one of, for example, a Universal Serial Bus (USB), a High Definition Multimedia Interface (HDMI), Recommended Standard 232 (RS-232), and a Plain Old Telephone Service (POTS). The network 162 may include at least one of a communication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. All or some of the operations performed in the electronic device 101 may be performed in another electronic device or a plurality of electronic devices 102, 104 or the server 106. When the electronic device 101 has to perform some functions or services automatically or in response to a request, the electronic device 101 may make a request for performing at least some functions relating thereto to another device 102, 104 or the server 106 instead of, or in addition to, performing the functions or services by itself. Another electronic device may execute the requested functions or the additional functions, and may deliver a result of the execution to the electronic device 101. The electronic device 101 may process the received result as is or additionally provide the requested functions or services. To achieve this, cloud computing, distributed computing, or client-server computing technology may be used.

Figure 2:
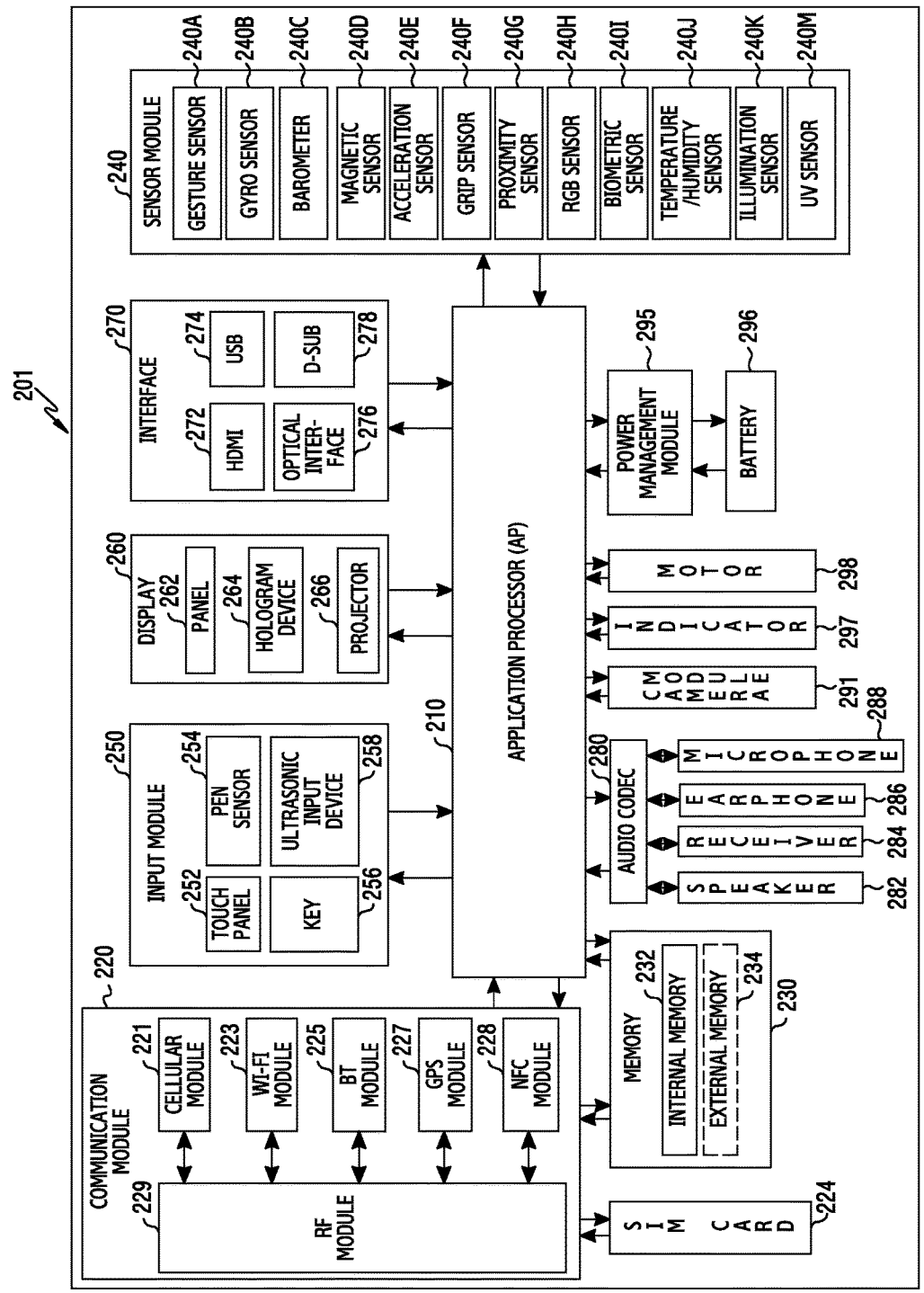
FIG. 2 illustrates a block diagram of an electronic device according to various embodiments of the present disclosure.

FIG. 2 illustrates a block diagram of an electronic device according to various embodiments of the present disclosure.

The electronic device 201 may include the entire or part of the electronic device 101 illustrated in FIG. 1. The electronic device 201 includes at least one processor (e.g., Application Processor (AP)) 210, a communication module 220, a Subscriber Identification Module (SIM) 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program and processing various pieces of data and calculations. The processor 210 may be implemented by a System on Chip (SoC). According to an embodiment of the present disclosure, the processor 210 may further include a Graphic Processing Unit (GPU) and/or an image signal processor. The processor 210 includes at least some (e.g., a cellular module 221) of the elements illustrated in FIG. 2. The processor 210 may load into a volatile memory, instructions or data received from at least one (e.g., a non-volatile memory) of the other elements and may execute instructions or process the data, and may store various data in a non-volatile memory.

The communication module 220 may have a configuration equal or similar to that of the communication interface 170 of FIG. 1. The communication module 220 includes the cellular module 221, a Wi-Fi module 223, a Bluetooth (BT) module 225, a GNSS module 227 (e.g., a GPS module, a Glonass module, a Beidou module, or a Galileo module), an NFC module 228, and a Radio Frequency (RF) module 229.

The cellular module 221 may provide a voice call, video call, a text message service, or an Internet service through, for example, a communication network. The cellular module 221 may distinguish between and authenticate electronic devices 201 within a communication network using a SIM card 224. According to an embodiment of the present disclosure, the cellular module 221 may perform at least some of the functions that the processor 210 may provide. The cellular module 221 may include a Communication Processor (CP).

Each of the Wi-Fi module 223, the BT module 225, the GNSS module 227, and the NFC module 228 may include, for example, a processor for processing data transmitted and received through the relevant module. At least some (e.g., two or more) of the cellular module 221, the Wi-Fi module 223, the BT module 225, the GNSS module 227, and the NFC module 228 may be included in one Integrated Chip (IC) or IC package.

The RF module 229 may transmit/receive, for example, a communication signal (for example, an RF signal). The RF module 229 may include, for example, a transceiver, a Power Amplifier Module (PAM), a frequency filter, a Low Noise Amplifier (LNA), and an antenna. At least one of the cellular module 221, the Wi-Fi module 223, the BT module 225, the GNSS module 227, and the NFC module 228 may transmit and receive RF signals through a separate RF module.

The SIM 224 may include, for example, a card including an embedded SIM, and may contain unique identification information (e.g., an Integrated Circuit Card Identifier (IC-CID)) or subscriber information (e.g., an International Mobile Subscriber Identity (IMSI)).

The memory 230 (for example, the memory 130) may include, for example, an internal memory 232 or an external memory 234. The embedded memory 232 may include at least one of a volatile memory (for example, a Dynamic Random Access Memory (DRAM), a Static RAM (SRAM), a Synchronous Dynamic RAM (SDRAM), and the like) and a non-volatile memory (for example, a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (for example, a NAND flash memory or a NOR flash memory), a hard disc drive, a Solid State Drive (SSD), and the like).

The external memory 234 may include a flash drive, for example, a Compact Flash (CF), a Secure Digital (SD), a Micro Secure Digital (Micro-SD), a Mini Secure Digital (Mini-SD), an eXtreme Digital (xD), a memory stick, and the like. The external memory 234 may be functionally and/or physically connected to the electronic device 201 through various interfaces.

The sensor module 240 may measure a physical quantity or detect an operation state of the electronic device 201, and may convert the measured or detected information into an electrical signal. For example, the sensor module 240 may include at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240II (for example, a Red/Green/Blue (RGB) sensor), a bio-sensor 240I, a temperature/humidity sensor 240J, a light sensor 240K, and an Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris sensor, a body fat sensor, and/or a fingerprint sensor. The sensor module 240 may further include a control circuit for controlling one or more sensors included therein. The electronic device 201 may further include a processor configured to control the sensor module 240 as a part of or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use at least one of, for example, a capacitive type, a resistive type, an infrared type, and an ultrasonic type. The touch panel 252 may also include a control circuit. The touch panel 252 may further include a tactile layer and provide a tactile reaction to the user.

The (digital) pen sensor 254 may include, for example, a recognition sheet which is part of the touch panel or is separated from the touch panel. The key 256 may include, for example, a physical button, an optical key or a keypad. The ultrasonic input device 258 may detect ultrasonic waves generated by an input tool through, a microphone 288 and identify data corresponding to the detected ultrasonic waves.

The display 260 (for example, the display 160) may include a panel 262, a hologram device 264 or a projector 266. The panel 262 may include a configuration that is identical or similar to the display 160 illustrated in FIG. 1. The panel 262 may be flexible, transparent, or wearable. The panel 262 and the touch panel 252 may be implemented as one module. The hologram 264 may show a three dimensional image in the air by using interference of light. The projector 266 may display an image by projecting light onto a screen. The screen may be located, for example, inside or outside the electronic device 201. The display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-subminiature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280 may bidirectionally convert a sound and an electrical signal. At least some elements of the audio module 280 may be included in, for example, the input/output interface 145 illustrated in FIG. 1. The audio module 280 may process sound information which is input or output through, for example, a speaker 282, a receiver 284, earphones 286, a microphone 288 and the like.

The camera module 291 is a device which may photograph a still image and a moving image. The camera module 291 may include one or more image sensors (for example, a front sensor or a back sensor), a lens, an Image Signal Processor (ISP) or a flash (for example, LED or xenon lamp).

The power management module 295 may manage, for example, power of the electronic device 201. The power management module 295 may include a Power Management Integrated Circuit (PMIC), a charger Integrated Circuit (IC), or a battery gauge. The PMIC may use a wired and/or wireless charging method. Examples of the wireless charging method may include, for example, a magnetic resonance method, a magnetic induction method, an electromagnetic method, and the like. Additional circuits (e.g., a coil loop, a resonance circuit, a rectifier, etc.) for wireless charging may be further included. The battery gauge may measure, for example, a remaining charge of the battery 296, and a voltage, a current, or a temperature during the charging. The battery 296 may include, for example, a rechargeable battery or a solar battery.

The indicator 297 may display a particular state (e.g., a booting state, a message state, a charging state, and the like) of the electronic device 201 or a part (e.g., the processor 210). The motor 298 may convert an electrical signal into mechanical vibration, and may generate vibration, a haptic effect, and the like. The electronic device 201 may include a processing unit (e.g., a GPU) for supporting a mobile television (TV). The processing unit for supporting mobile TV may, for example, process media data according to a certain standard such as Digital Multimedia Broadcasting (DMB), Digital Video Broadcasting (DVB), or MediaFLO™.

Each of the above-described component elements according to the present disclosure may be configured with one or more components, and the names of the corresponding component elements may vary based on the type of electronic device. The electronic device according to various embodiments of the present disclosure may include at least one of the aforementioned elements. Some elements may be omitted or other additional elements may be further included in the electronic device. Also, some of the components according to various embodiments may be combined into one entity, which may perform functions identical to those of the relevant components before the combination.

Figure 3:
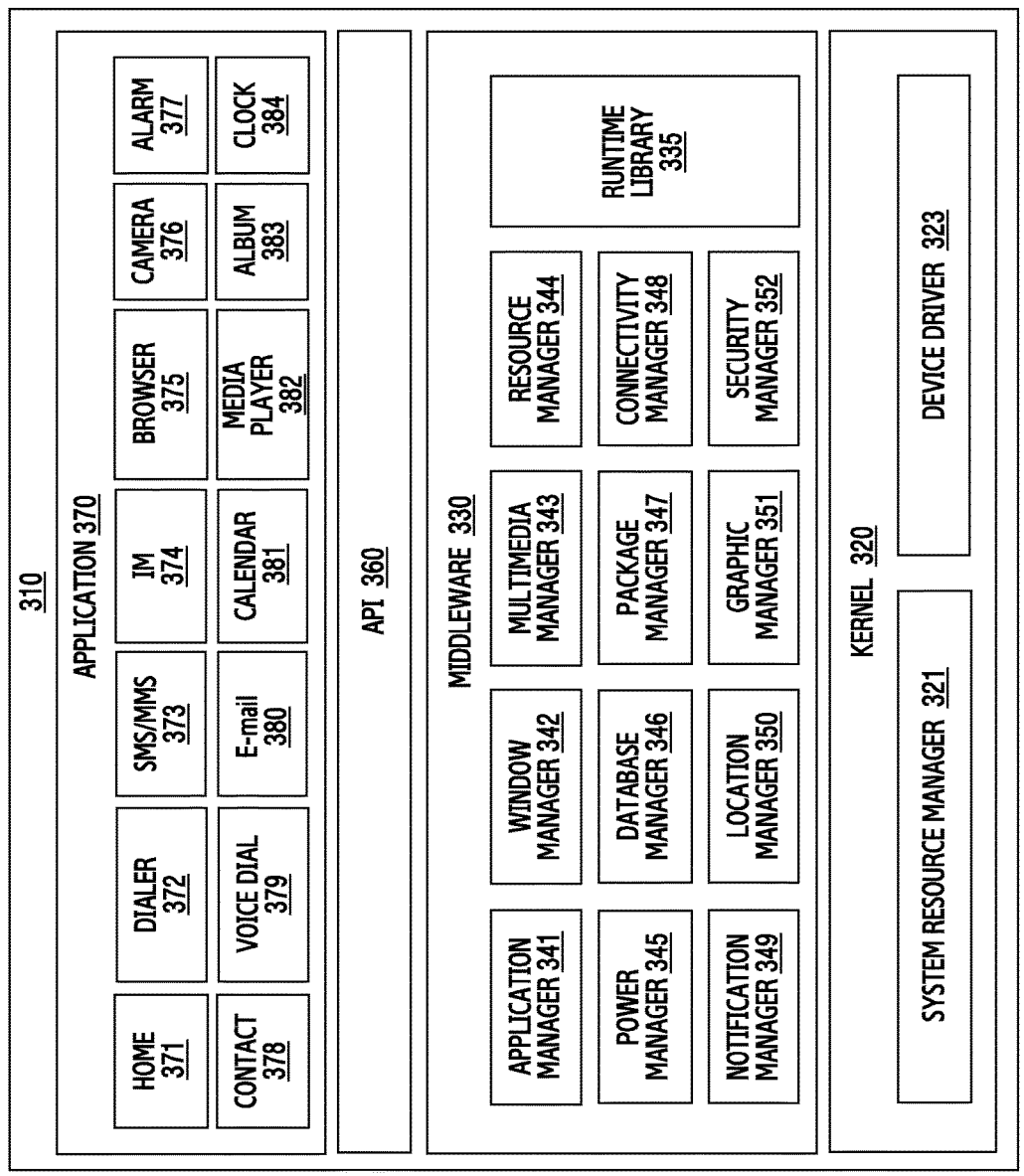
FIG. 3 illustrates a block diagram of a program module according to various embodiments of the present disclosure.

FIG. 3 illustrates a block diagram of a program module according to various embodiments of the present disclosure.

According to an embodiment of the present disclosure, the program module 310 (for example, the program 140) may include an Operating System (OS) for controlling resources related to the electronic device (for example, the electronic device 101) and/or various applications (for example, the application programs 147) executed in the operating system. The operating system may be, for example, Android, iOS, Windows, Symbian, Tizen, Bada, and the like.

The program module 310 includes a kernel 320, middleware 330, an API 360, and/or an application 370. At least some of the program module 310 may be preloaded on the electronic device 101, or may be downloaded from an external electronic device 102, 104, or the server 106.

The kernel 320 (e.g., the kernel 141) includes, for example, a system resource manager 321 and/or a device driver 323. The system resource manager 321 may perform the control, allocation, retrieval, and the like of system resources. According to an embodiment of the present disclosure, the system resource manager 321 may include a process manager, a memory manager, a file system manager, and the like. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

The middleware 330 may provide a function required by the application 370 in common or provide various functions to the application 370 through the API 360 so that the application 370 may efficiently use limited system resources within the electronic device 101. The middleware 330 (for example, the middleware 143) includes, for example, at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while the applications 370 are being executed. The runtime library 335 may perform input/output management, memory management, the functionality for an arithmetic function, and the like.

The application manager 341 may manage, for example, the life cycle of at least one of the applications 370. The window manager 342 may manage Graphical User Interface (GUI) resources used for the screen. The multimedia manager 343 may determine a format required to reproduce various media files, and may encode or decode a media file by using a coder/decoder (codec) appropriate for the relevant format. The resource manager 344 may manage resources, such as a source code, a memory, a storage space, and the like of at least one of the applications 370.

The power manager 345 may operate together with a Basic Input/Output System (BIOS) to manage a battery or power and may provide power information required for the operation of the electronic device 101. The database manager 346 may generate, search for, and/or change a database to be used by at least one of the applications 370. The package manager 347 may manage the installation or update of an application distributed in the form of a package file.

The connectivity. manager 348 may manage a wireless connection such as Wi-Fi or Bluetooth. The notification manager 349 may display or notify of an event, such as an arrival message, an appointment, a proximity notification, and the like, in such a manner as not to disturb the user. The location manager 350 may manage location information of the electronic device 101. The graphic manager 351 may manage a graphic effect, which is to be provided to the user, or a user interface related to the graphic effect. The security manager 352 may provide various security functions required for system security, user authentication, and the like. According to an embodiment of the present disclosure, when the electronic device 101 has a telephone call function, the middleware 330 may further include a telephony manager for managing a voice call function or a video call function of the electronic device.

The middleware 330 may include a middleware module that forms a combination of various functions of the above-described elements. The middleware 330 may provide a module specialized for each type of OS in order to provide a differentiated function. The middleware 330 may dynamically delete some of the existing elements, or may add new elements.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (for example, the application program 147) include, for example, one or more applications which may provide functions such as home 371, dialer 372, SMS/MMS 373, Instant Message (IM) 374, browser 375, camera 376, alarm 377, contacts 378, voice dialer 379, email 380, calendar 381, media player 382, album 383, clock 384, health care (for example, measure exercise quantity, body fat impedance, body fat percentage or blood sugar), or environment information (for example, atmospheric pressure, humidity, or temperature information).

According to an embodiment of the present disclosure, the application 370 may include an application (hereinafter, referred to as an "information exchange application") supporting information exchange between the electronic device 101 and an external electronic device 102, 104. The application associated with information exchange may include, for example, a notification relay application for forwarding specific information to an external electronic device, or a device management application for managing an external electronic device.

For example, the notification relay application may include a function of delivering to the external electronic device 102, 104, notification information generated by other applications (e.g., an SMS/MMS application, an email application, a health care application, an environmental information application, etc.) of the electronic device 101. Further, the notification relay application may receive notification information from, for example, an external electronic device and provide the received notification information to a user.

The device management application may manage (for example, install, delete, or update), for example, a function for at least a part of the external electronic device 102, 104 communicating with the electronic device (for example, turning on/off the external electronic device itself (or some elements thereof) or adjusting brightness (or resolution) of a display), applications executed in the external electronic device, or services provided from the external electronic device (for example, a telephone call service or a message service).

According to an embodiment of the present disclosure, the applications 370 may include applications (for example, a health care application of a mobile medical appliance and the like) designated according to attributes of the external electronic device 102 or 104. The application 370 may include an application received from the external electronic device 102, 104 or the server 106. The application 370 may include a preloaded application or a third party application which may be downloaded from the server 106. Names of the elements of the program module 310, according to the above-described embodiments of the present disclosure, May change depending on the type of OS.

According to various embodiments of the present disclosure, at least some of the program module 310 may be implemented in software, firmware, hardware, or a combination of two or more of them. At least some of the program module 310 may be implemented (e.g., executed) by, for example, the processor (e.g., the processor 210). At least some of the program module 310 may include, for example, a module, a program, a routine, a set of instructions, and/or a process for performing one or more functions.

The term "module" as used herein may, for example, refer to a unit including one of hardware, software, and firmware or a combination of two or more of them. The term "module" may be interchangeably used with, for example, the term "unit", "logic", "logical block", "component", or "circuit". The "module" may be a minimum unit of an integrated component element or a part thereof. The "module" may refer to a minimum unit for performing one or more functions or a part thereof. The "module" may be mechanically or electronically implemented. For example, the "module" may include at least one of an Application-Specific Integrated Circuit (ASIC) chip, a Field-Programmable Gate Arrays (FPGA), and a programmable-logic device for performing.

According to various embodiments of the present disclosure, at least some of the devices (for example, modules or functions thereof) or the methods (for example, operations) may be implemented by a command stored in a computer-readable storage medium in a programming module form. The command, when executed by a processor (e.g., the processor 120), may cause the one or more processors to execute the function corresponding to an instruction. The computer-readable storage medium may be, for example, the memory 130.

The computer readable recording medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high level language codes, which may be executed in a computer by using an interpreter, as well as machine codes made by a compiler. The aforementioned hardware device may be configured to operate as one or more software modules in order to perform the operation of the present disclosure, and vice versa.

The programming module according to an embodiment of the present disclosure may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added. The exemplary embodiments disclosed herein are suggested for describing and understanding the disclosed technical contents, and do not limit the scope of the technology described in the present disclosure. Accordingly, the scope of the present disclosure should be construed as including all modifications or various other embodiments based on the technical idea of the present disclosure.

The electronic device 101 according to various embodiments of the present disclosure may include all devices which use one or more various processors 120 and 210, such as an Application Processor (AP), a Communication Processor (CP), a Graphic Processing Unit (GPU), and a Central Processing Unit (CPU), like all information communication devices, multimedia devices, wearable devices, and application devices thereon, which support functions according to various embodiments of the present disclosure.

In various embodiments explained herein below, a hardware method will be explained by way of example. However, various embodiments of the present disclosure include technology Using both hardware and software, and thus do not exclude a software-based method.

The electronic device 101 may have a sensor (health care sensor) mounted therein to measure human body information of a user. The user may measure human body information and manage the measured human body information through the electronic device 101. The health care function of the electronic device 101 is to manage an individual's health and prevent diseases, rather than to cure diseases. The health care sensor may be a blood glucose sensor, an acceleration sensor (for example, a pedometer), a heart rate sensor, a blood pressure sensor, a pulse rate sensor, a body fat sensor, an electrocardiogram sensor, etc.

The body composition refers to composition constituting a human body, and may indicate body water, protein, body fat, minerals, etc. Obesity normally refers to an overweight state, and more specifically, refers to a state in which body fat mass is relatively greater than muscle mass. There are various methods for measuring the body composition, such as underwater weighing, Dual Energy X-ray Absorptiometry (DEXA), Biological Impedance Analysis (BIA), skin fold technique, etc. The BIA, which calculates an amount of body fat using the body's bioelectrical impedance which is relatively simple and accurate, is mainly used as a method for measuring body fat. The BIA is a method for measuring bioelectrical impedance of a human body, and normally uses four electrodes to measure body composition, and may include an entire body 4-electrode and 2-point or upper body 4-electrode and 2-point method. The 4-electrode and 2-point measuring method reduces measurement error. For example, the upper body 4-electrode and 2-point measurement method may cause a measurement error according to a user's hand shape or a muscle shape. In addition, when the measurement device measures body fat while the user uses both hands, a predetermined time may be required to maintain a stable posture. Therefore, the body fat measurement method may require a user to maintain the same posture every time it measures. The electronic device 101 may include a camera module 291. According to various embodiments of the present disclosure, when measuring human body information, the electronic device 101 may display a guide image on the display 160 or 260, and automatically start measuring when the posture of a user (a person to be measured) is consistent with the measurement posture of the guide image. In addition, the electronic device 101 may photograph the image of the person to be measured when measuring, and manage the image with measured user human body information. Therefore, the electronic device 101 may suggest a guide image in order to reduce a measurement error when measuring human body information, and may form a database by storing the change in the human body information, the image, and measuring date.

Figure 4:
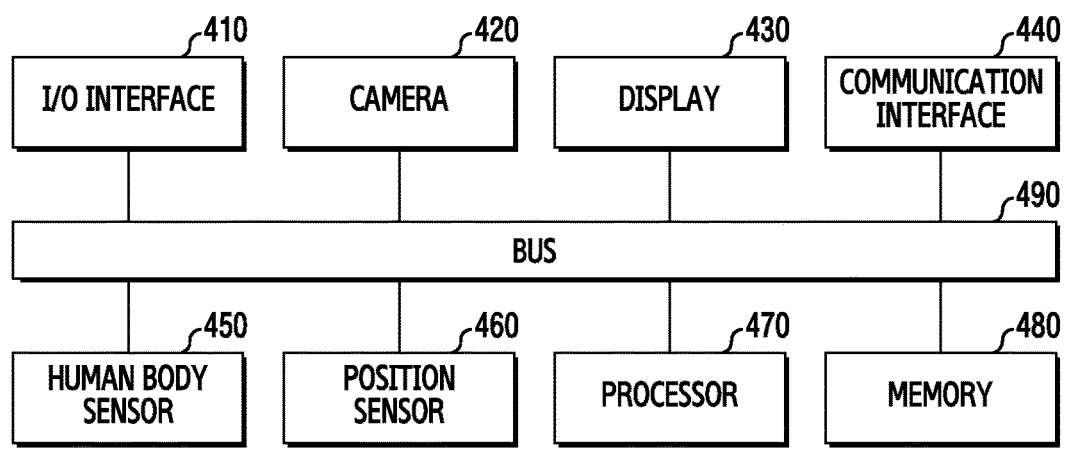
FIG. 4 illustrates a block diagram of another electronic device including a camera according to various embodiments of the present disclosure.

FIG. 4 illustrates a block diagram of another electronic device including a camera according to various embodiments of the present disclosure.

Referring to FIG. 4, the electronic device 101 according to various embodiments of the present disclosure includes a processor 470, an I/O interface 410, a camera 420, a display 430, a communication interface 440, a human body sensor 450, a position sensor 460, and a memory 480. The electronic device 101 may omit at least one of the elements or may further include other elements. The I/O interface 410 may provide input and output signals to the electronic device 101. The I/O interface 410 may be the input device 250 or interface 270 of FIG. 2. The camera 420 may photograph a still or moving image of a user (a person to be measured) when human body information is measured. The camera 420 may be the camera module 291 of FIG. 2. The display 430 may display a guide image when human body information is measured. In addition, the display 430 may display the image of the person to be measured, which is photographed by the camera 420, with the guide image. The display 430 may be the display 260 of FIG. 2. The communication interface 440 may provide a communication function between the electronic device 101 and an external device. The communication interface 440 may be the communication module 220 of FIG. 2. For example, the communication interface 440 may receive or transmit human body information data.

The human body sensor 450 may be a sensor for detecting human body information. That is, the human body sensor 450 may detect a blood pressure, temperature, impedance, etc. of a human body. For example, the human body sensor 450 may be a body fat sensor. The body fat sensor may measure body fat by measuring human body impedance. The body fat sensor may include four electrodes for measuring body fat or electrocardiography (ECG). The four electrodes of the body fat sensor may be mounted on a side surface of the electronic device 101. Two of the four electrodes of the body fat sensor may be mounted on the side surface of the electronic device 101, and the other two may be mounted on the rear surface of the electronic device 101. The human body sensor 450 may be the biosensor 2401 included in the sensor module 240 of FIG. 2. The position sensor 460 may be a sensor for detecting the position of the electronic device 101. The position of the electronic device 101 may be a reference position for executing a landscape display mode or a portrait display mode. The position sensor 460 may be the gyro sensor 240B and/or the acceleration sensor 240E included in the sensor module 240. The processor 470 may execute a program for measuring human body information. When a human body measurement request is detected, the processor 470 may display a guide or a guide image on the display 430, and drive the camera 420. In addition, when an image of a person to be measured, which is photographed by the camera 420, corresponds to (is consistent with or overlaps with) the guide image, the processor 470 may process or analyze human body information detected by the human body sensor 450. For example, the processor 470 may measure impedance of a human body through the human body sensor 450, and may analyze body composition (body fat, body water, minerals, etc.) from the impedance measurement. In addition, the processor 470 may store the result of the analysis in the memory 480. The processor 470 may be the processor 210 of FIG. 2.

The memory 480 may store the guide image, and the guide image may be accessed by the processor 470. The guide image may be formed of images corresponding to the landscape display mode or the portrait display mode. In addition, the memory 480 may store the image of the user (person to be measured) photographed under the control of the processor 470, and the measured and analyzed human body information. In addition, the memory 480 may store other information during measurement, as well as the image of the person to be measured and the processed human body information. For example, the processor 470 may store information detected by sensors, such as current temperature, posture, location, environment information, etc., in the memory 480. The memory 480 may be the memory 230 of FIG. 2.

Referring to FIG. 4, when a human body measurement request signal is generated through the I/O interface 410, the processor 470 may display the guide image on the display 430 and activate the camera 420, the human body sensor 450, and the position sensor 460 to measure the human body information. In addition, the processor 470 may process the image photographed in the camera 420, and display the image of the person to be measured on the display 430 in real time.

Figure 5A:
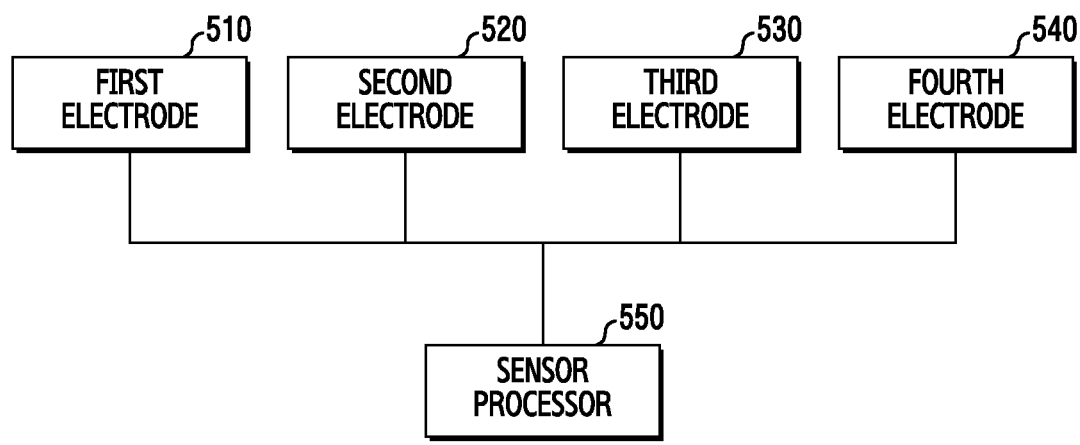
FIGS. 5A to 5E illustrate a configuration of a sensor and a sensor mounted on an electronic device according to various embodiments of the present disclosure.
Figure 5B:
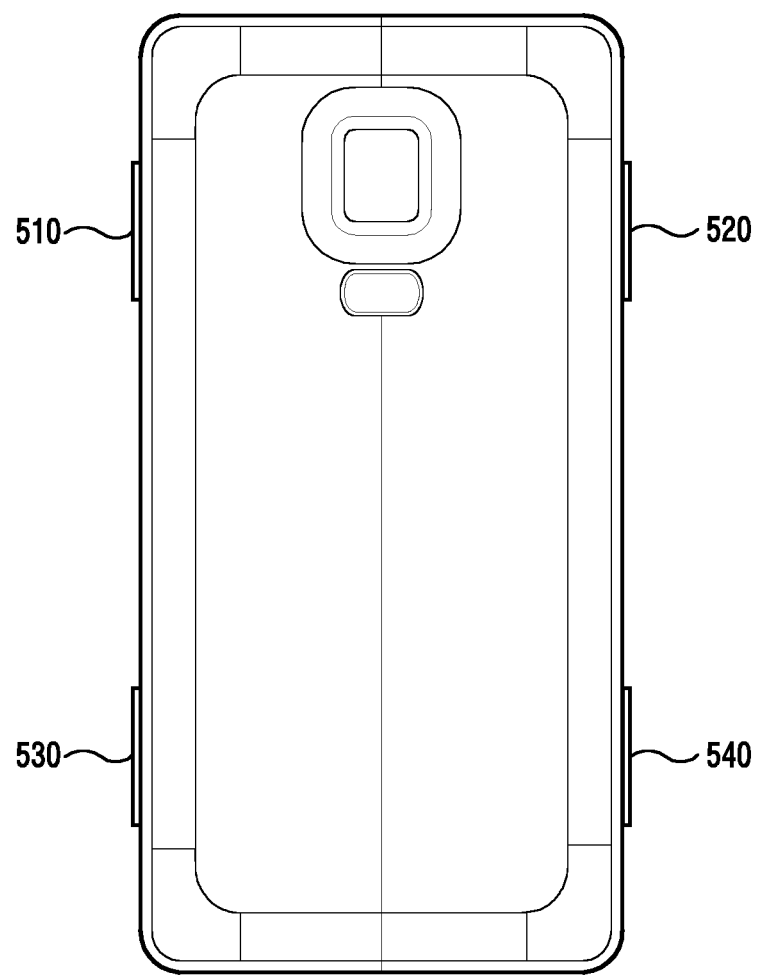
Figure 5C:
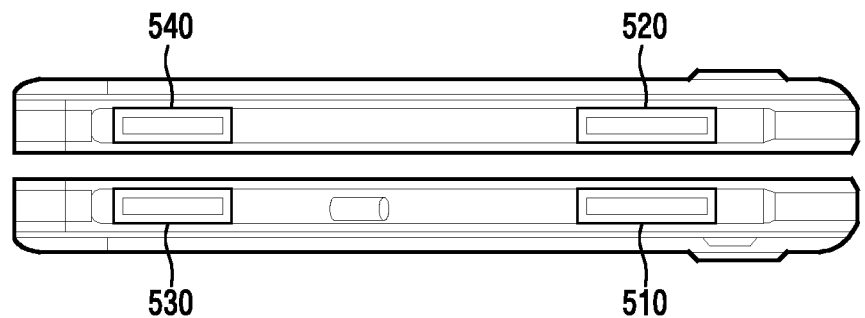
Figure 5D:
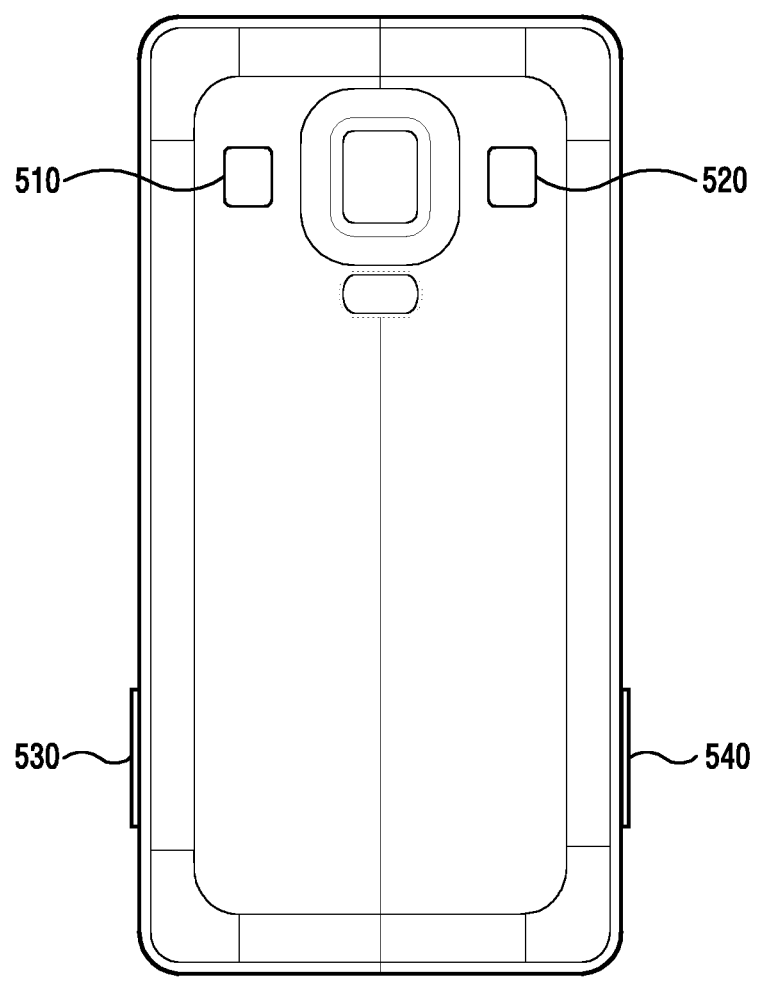

The electronic device 101 may perform a measuring operation by analyzing the guide image and the image of the person to be measured, which is displayed. For example, when body fat is measured, a measurement error may occur according to the hand shape or the muscle shape of the user. In addition, when measurement is made using both hands, it may be necessary to have both hands stop for a predetermined time after a measurement signal was generated. In order to prevent such a measurement error from occurring, it may be preferable to guide the user to maintain the same posture. Therefore, the electronic device 101 may display the guide image on the display 430 to instruct the user in a correct measurement posture. For example, the processor 470 may display a guide image expressing the appearance of a human body as a solid line or a dashed line on the display 430. In addition, the processor 470 may display the image of the person to be measured, which is acquired by the camera 420, on the display while a human body measurement mode is being executed. In addition, when the displayed image of the person to be measured and the guide image correspond to each other (are consistent with each other or overlap each other), the processor 470 may automatically start the human body measuring operation. In addition, when measurement is made again, the electronic device 101 may use the captured image of the person to be measured as a guide image. FIGS. 5A to 5E illustrate a configuration of a sensor and a sensor mounted on an electronic device according to various embodiments of the present disclosure. The sensor illustrated in FIGS. 5A to 5E may be a body fat sensor with four electrodes. FIG. 5A illustrates a configuration of a human body sensor 450 including four electrodes. The four electrodes create four electrode points on the electronic device 101. The body fat sensor may require four or more electrodes into which the user's fingers are brought into contact. The body fat sensor may use four or eight electrodes, and FIG. 5A illustrates a sensor with four electrodes 510, 520, 530 and 540. FIGS. 5B to 5D illustrate electrodes which are mounted in the electronic device 101. FIG. 5B illustrates a rear view showing the positions of the four electrodes 510, 520, 530 and 540 installed on the side surfaces of the electronic device 101. FIG. 5B illustrates an example of the four electrodes in total installed in the electronic device 101. Two of them, 520 and 540 are installed on the right side surface and the other two, 510 and 530 are installed on the left side surface. FIG. 5C illustrate a side view showing the positions of the four electrodes 510, 520, 530, and 540 installed on the side surfaces of the electronic device 101. Two of the electrodes 510 to 540 may be installed on each of the left and right side surfaces, and the positions of the respective electrodes may be set in positions where the user may be measured in a stable posture.

Figure 5E:
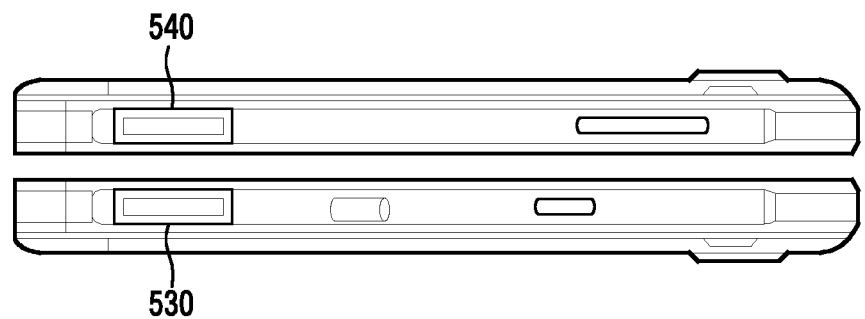

FIG. 5D illustrates a rear view showing the positions of the four electrodes 510, 520, 530 and 540 installed on the rear surface and the side surfaces of the electronic device 101. As shown in FIG. 5D, two electrodes 510 and 520 of the four electrodes may be installed on the rear surface and the other two electrodes 530 and 540 may be installed on the side surfaces. FIG. 5E illustrates a side view showing the positions of the two electrodes 530 and 540 installed on the side surfaces of the electronic device 101. That is, the electrodes may be installed on the left and right side surfaces.

As shown in FIGS. 5B and 5C or 5D and 5E, the electrodes may be arranged on both side surfaces of the electronic device 101 as sensors. As described above, the electrodes of the electronic device 101 may be arranged so that the person to be measured may spread out their arms by a predetermined distance and maintain a posture for effectively measuring the body fat. In addition, the electronic device 101 may provide an instructing guide to the person to be measured when measuring the body fat, so that a measurement error may be reduced.

When human body information such as body fat is measured, the person to be measured may be required to maintain the same posture during measurement (for example, a posture in which the user spreads out their arms by a predetermined distance). The electronic device 101 may display an image guiding the user on the correct measurement posture when measuring human body information. The guide image may be displayed differently according to a display mode of the electronic device 101 (for example, a landscape display mode or a portrait display mode). The guide image of the electronic device 101 may include guide images of a portrait or landscape mode. In addition, the electronic device 101 may detect a display mode according to the position of the electronic device 101 in the human body measurement mode, and display a guide image corresponding to the detected display mode.

Figure 6A:
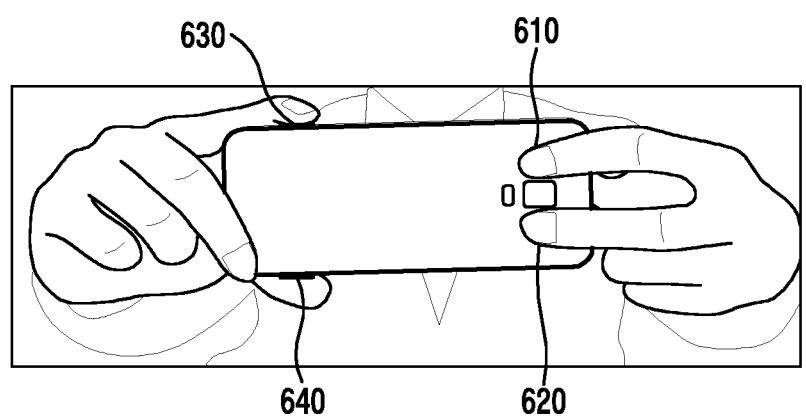
FIGS. 6A to 6C illustrate a method for measuring human body information in a landscape display mode of an electronic device according to various embodiments of the present disclosure.
Figure 6B:
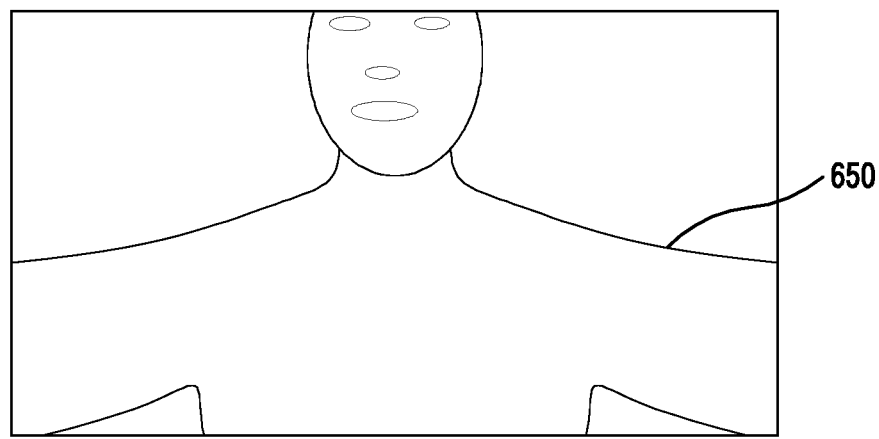
Figure 6C:
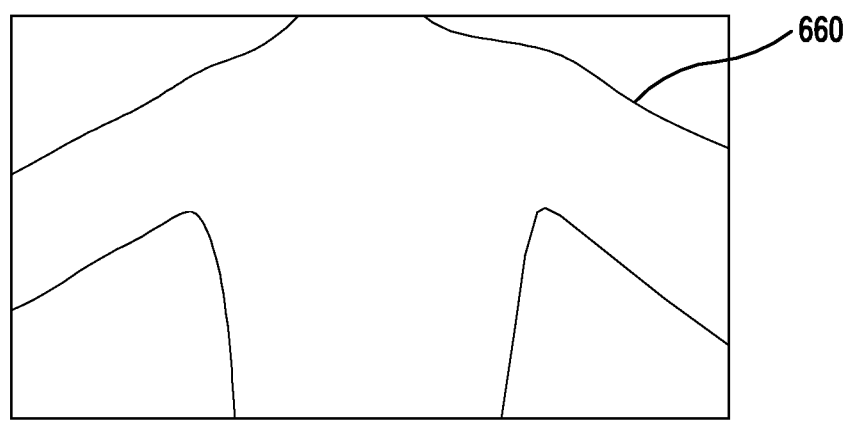

FIGS. 6A to 6C illustrate a method for measuring human body information in a landscape display mode of an electronic device according to various embodiments of the present disclosure.

FIG. 6A illustrates a method for measuring human body information with the electronic device 101 being gripped in a landscape state. FIG. 6A illustrates two electrodes 610 and 620 which are installed on the rear surface of the electronic device 101, and two electrodes 630 and 640 which are installed on side surfaces of the electronic device 101. When the person to be measured grips the electronic device 101 as shown in FIG. 6A, the position sensor 460 (for example, a gyroscope sensor, an acceleration sensor, etc.) of the electronic device of FIG. 4 may generate information related to the position of the electronic device 101, and the processor 470 may analyze the output of the position sensor 460 and detect that the electronic device 101 is gripped in the landscape state. When it is detected that the electronic device 101 is gripped in the landscape state, the processor 470 may access a guide image of a landscape type in the memory 480, and display the guide image on the display 430. FIGS. 6B and 6C illustrate guide images which are displayed on the display 430 when measurement is made in the landscape mode. FIG. 6B illustrates a guide image 650 including the face of the person to be measured and displaying the upper body and FIG. 6C illustrates a guide image 660 which does not include the face of the person to be measured and displays only the upper body. The person to be measured may select one of the guide images shown in FIG. 6B or 6C, and use the selected guide image.

Figure 7A:
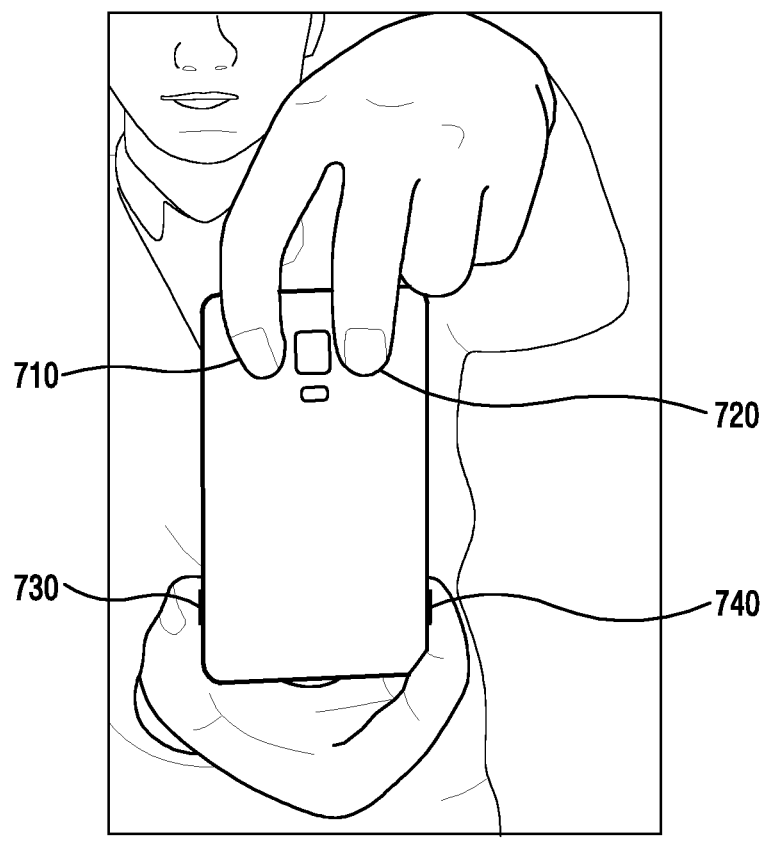
FIGS. 7A and 7B illustrate a method for measuring human body information in a portrait display mode of an electronic device according to various embodiments of the present disclosure.
Figure 7B:
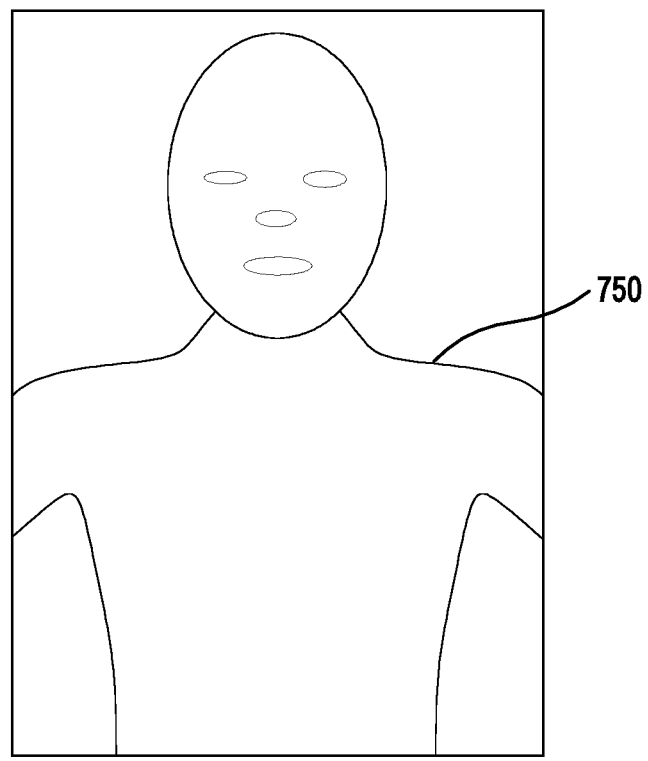

FIGS. 7A and 7B illustrate a method for measuring human body information in a portrait display mode according to various embodiments of the present disclosure.

FIG. 7A illustrates a method for measuring human body information with an electronic device being gripped in a portrait state. FIG. 7A illustrates a view showing an example of the electronic device 101 which has two electrodes 710 and 720 installed on the rear surface thereof, and two electrodes 730 and 740 installed on the side surfaces thereof, and which is gripped in the portrait state.

When it is detected that the electronic device 101 is gripped in the portrait state, the processor 470 of FIG. 4 may access a guide image of a portrait type in the memory 480, and display the guide image on the display 430. FIG. 7B illustrates a guide image 750 displayed on the display when measurement is made in the portrait mode.

The user may select one of the landscape mode and the portrait mode to measure human body information (for example, a body fat percentage), and may select according to a measurement method the user desires, or according to which part of the upper body the user wishes to observe in detail.

The guide image may help the user maintain a stable posture while measuring human body information (for example, impedance). For example, when body fat is measured, a measurement value may change according to the posture of the person to be measured. This is because the measurement posture is changed during the measurement and thus an error may occur. The guide image helps the user maintain the stable measurement posture, so that reliable measurement values of human body information (for example, impedance) may be obtained at each time period, and the accuracy of measurement of human body information (for example, body fat) may be increased.

As described above, when a human body measurement request signal is generated, the processor 470 of FIG. 4 may access a guide image of a corresponding human body measurement mode in the memory 480, and display the guide image on the display 430. In this case, the guide image may vary according to the position of the electronic device 101. The processor 470 may analyze the output of the position sensor 460 and determine the position (landscape or portrait position) of the electronic device 101. In addition, the electronic device 101 may access a landscape guide image in the memory 480 in the landscape display mode, and display the guide image, and may access a portrait guide image in the memory 480 in the portrait display mode and display the guide image. The guide image may be an image for guiding correct measurement posture, and the processor 470 of FIG. 4 may display additional information (for example, text information explaining a measurement posture, etc.) when displaying the guide image. In addition, the guide image may be an image which expresses the appearance of a human body in a solid line or a dashed line. In addition, the processor 470 may display the guide image on the display 430 when measuring human body information, and may acquire an image of the person to be measured by driving the camera 420.

The processor 470 of FIG. 4 may analyze the image of the person to be measured and the guide image by comparing them, and automatically perform the measuring operation when the person to be measured maintains the stable posture. When the photographed image of the person to be measured is located within a predetermined area of the guide image (for example, the image of the person to be measured and the guide image correspond to each other (are consistent with or overlap with each other), the processor 470 may determine that the person to be measured is maintaining the stable measurement posture, and analyzes the human body information detected by the human body sensor 450. The electronic device 101 may automatically start measuring human body information when the image of the person to be measured, which is photographed during the measurement, corresponds to the guide image (is consistent with or overlaps with the guide image). In addition, when human body information is measured, the processor 470 may capture the image of the person to be measured, which is photographed by the camera 420, and store the captured image. The processor 470 may access the stored image of the person to be measured when next measuring human body information, and display the image as a guide image.

When the guide image is displayed, the processor 470 may drive the camera 420, and may process the image photographed by the camera 420 and display the image on the display 430. In addition, when the image of the person to be measured is consistent with (or corresponds to) the guide image within a predetermined range, the processor 470 may analyze human body information detected by the human body sensor 450. The photographed image of the person to be measured may be consistent with the guide image when the measurement posture of the person to be measured is stable. Therefore, when the photographed image of the person to be measured is consistent with (or corresponds to) the guide image, the processor 470 may determine that the measurement posture is stable and perform the human body measuring operation. When the human body measuring operation is performed, the processor 470 may analyze the human body information detected by the human body sensor 450, and display the result of the analysis on the display. In addition, when the human body information measuring operation is performed, the processor 470 may capture the image from the camera 420 and store the captured image in the memory 480. In this case, the captured image may be a still image or a moving image.

Figure 8:
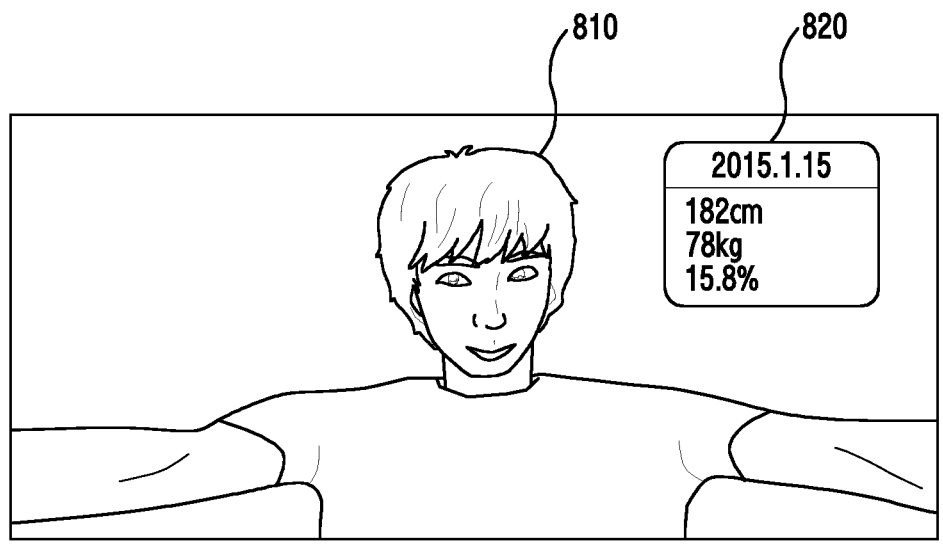
FIG. 8 illustrates a display of human body information in an electronic device according to various embodiments of the present disclosure.

FIG. 8 illustrates a display of human body information in an electronic device according to various embodiments of the present disclosure. FIG. 8 illustrates an example of displaying a result of measurement of human body information.

Referring to FIG. 8, the processor 470 may display an image 810 of a person to be measured which is from the camera 420, and measured human body information 820 on the display 430 while measuring human body information. For example, the human body information may be a result of measurement of body fat. In addition, the displayed human body information may be displayed with other data such as a measuring date, a muscle mass, body water, as well as height, weight, and a body fat percentage. In addition, the human body information and the image of the person measured may be stored in the memory 480 with the measuring date.

The person to be measured may observe his/her appearance by comparing the weight and the body fat percentage using the resulting image of the measurement. That is, the person to be measured may know changes in his/her body fat percentage and body shape at each measurement period by observing his/her appearance which is changed according to the body fat percentage according to the measuring date.

Figure 9:
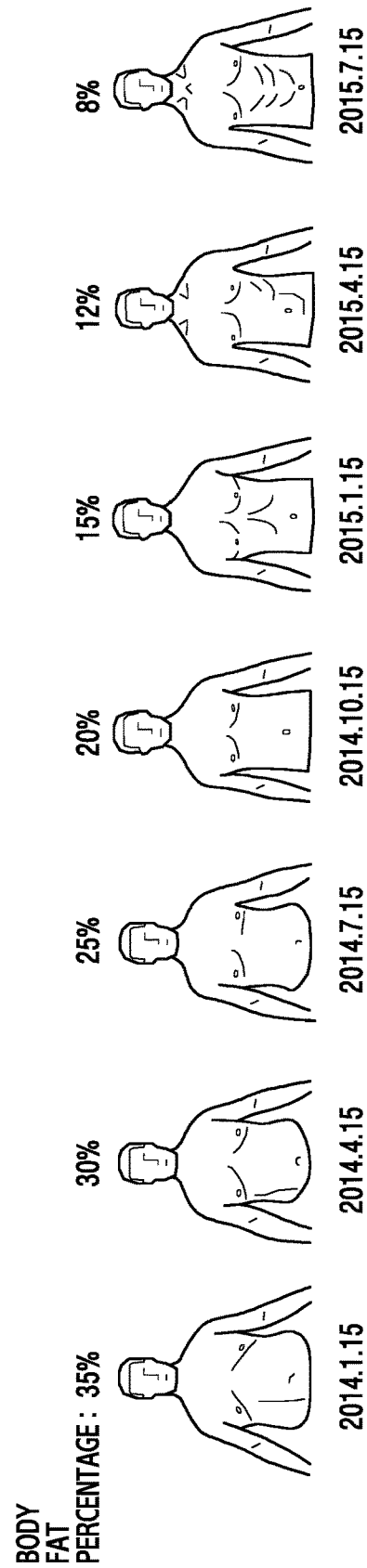
FIG. 9 illustrates content of a database which is formed by storing resulting images of measurements of body fat percentage according to measuring date according to various embodiments of the present disclosure.

In addition, the data stored after being measured may be stored not only as the image but also as body composition data. The body composition data may be stored as a text file and/or an Excel file according to measuring date in order for the user to process the data. In addition, the measuring date, body fat percentage, body composition, etc. may be processed as metadata and stored for easy classification. FIG. 9 illustrates content of a database which is formed by storing resulting images of measurements of a body fat percentage according to measuring date according to various embodiments of the present disclosure.

Referring to FIG. 9, the electronic device 101 may store measured human body information. Therefore, the electronic device 101 may form a database by storing a body fat percentage according to measuring date, and a captured image of a person to be measured, and may effectively manage human body information. In addition, the electronic device 101 may manage other body composition data (for example, a muscle mass, body water, and minerals) as data instead of, or in addition to, the body fat percentage. The electronic device 101 informs the user of a user's body fat percentage and change in the body shape at each measurement period, so that the user may systematically manage their health and body shape.

According to various embodiments of the present disclosure, the electronic device 101 may include the human body sensor 450 to detect human body information, the camera 420 to photograph an image of a person to be measured, the display 430 to display a guide image and the image of the person to be measured, and the processor 470 to display the guide image in a measurement mode, display the image of the person to be measured, which is photographed by the camera, and start and display a human body measuring operation when the image of the person to be measured is located within (or corresponds to) the guide image.

The human body sensor 450 of the electronic device 101 may be a body fat measuring sensor. In addition, the human body sensor 450 may be a four-electrode sensor which is mounted on the side surface of the electronic device 101. In addition, the human body sensor 450 may be a four-electrode sensor having two electrodes mounted on the side surface thereof and the other two electrodes mounted on the rear surface thereof.

The processor 470 of the electronic device 101 may receive an input of human body information measurement mode of the user when a touch on the electrode of the human body sensor 450 is detected, display a guide to the user, drive the camera, and acquire a photographed image. The processor 470 may further receive input from position sensor 460 to identify the position of the electronic device 101, and may display the guide image according to the position of the electronic device 101 detected by the position sensor 460. In addition, the processor 470 may display the guide image when the electrode of the human body sensor is touched as well as when the input for the human body information measurement is received.

The processor 470 may identify a landscape display mode or a portrait display mode by analyzing the output of the position sensor 460, and display a guide image corresponding to the identified display mode. The processor 470 may capture an image which is photographed by the camera during the measurement of the body fat value, and store the measured body fat value with the photographed image after finishing the body fat measurement. The processor 470 may display an image which was photographed in a previous measurement mode as a guide image when displaying the guide image.

The electronic device according to various embodiments of the present disclosure may include the human body sensor 450 to detect human body information, the camera 420 to photograph a human body image, the display 430 to display a guide image and the human body image, and the processor 470 to measure a human body when the human body image corresponds to the guide image, and output a result of the measurement of the human body.

The human body sensor 450 may be a body fat measuring sensor. In addition, the human body sensor 450 may be a four-electrode sensor which is mounted on a plurality of side surfaces of the electronic device 101. The human body sensor 450 may be a four-electrode sensor having two electrodes mounted on a plurality of side surfaces of the electronic device 101 and two electrodes mounted on a rear surface of the electronic device 101. When a touch is detected by the human body sensor 450, the processor 470 may display the guide image and acquire a photographed image.

The processor 470 may further include the position sensor 460 to identify the position of the electronic device 101, and when a touch is detected by the human body sensor 450, the processor 470 may display the guide image according to the position of the electronic device 101 detected by the position sensor 460. The processor 470 may identify a landscape display mode or a portrait display mode by analyzing an output of the position sensor 460, and display the guide image according to the identified display mode. The processor 470 may capture the human body image photographed by the camera 420, and measure body fat based on the guide image and the human body image.

The processor 470 may map and store the human body image and the measured body fat, and when a result of the measurement of the body fat is requested, may output the stored human body image and measured body fat measurement.

The processor 470 may display a human body image which was previously captured as the guide image.

Figure 10:
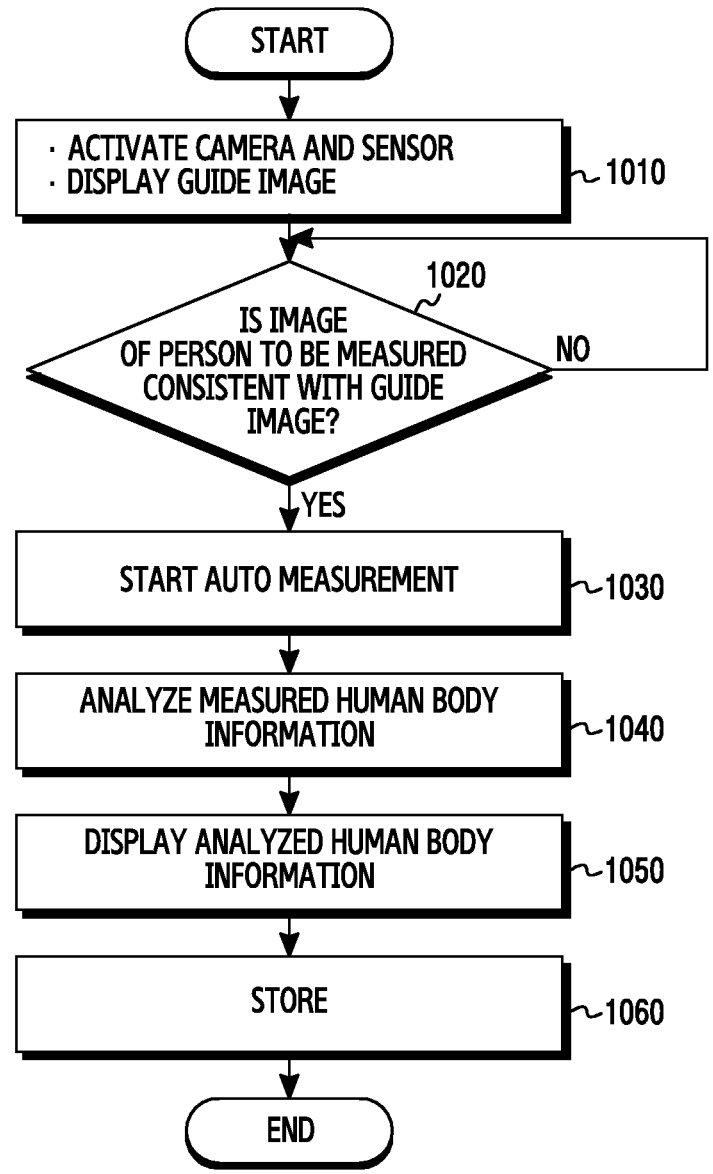
FIG. 10 illustrates a flowchart of a method for measuring human body information using a camera according to various embodiments of the present disclosure.

FIG. 10 illustrates a flowchart of a method for measuring human body information using a camera according to various embodiments of the present disclosure.

Referring to FIGS. 4 and 10, when a human body measurement mode is requested, the electronic device 101 activates the operations of the human body sensor 450, the position sensor 460, and the camera 420 in step 1010. In addition, in step 1010, the electronic device 101 displays a guide image on the display 430 as shown in FIGS. 6B, 6C, and 7B. The human body measurement mode may be executed when the user selects a human body information measurement mode through the I/O interface 410, or touches the electrodes of the human body sensor 450. The electronic device 101 may access a guide image in the memory 480 and display the guide image on the display 430. In this case, the guide image may be an image which is set as default. In addition, the guide image may be an image of a person to be measured, which was photographed previously. The electronic device 101 may store guide images for measuring human body information as default images. In addition, the electronic device 101 may use an image of a user which was photographed when previous human body information was measured as a guide image. The electronic device 101 may use the default guide image or the photographed image of the user as a guide image when measuring human body information.

When the camera 420 is activated, the electronic device 101 may process the image of the person to be measured, which is photographed by the camera 420, and display the image on the display 430 in real time. When body fat is measured for the first time, a window for requesting input of height and weight may be displayed. In addition, when the body fat is measured for the second time and the height and weight are changed, the user (person to be measured) may directly input user's height and weight. When the camera 420 is driven, the electronic device 101 may display the guide image and the image of the person to be measured, which is photographed by the camera 420, on the display 430. In this case, the user may correct the posture of the person to be measured to be consistent with (or correspond to) the guide image displayed on the display 430. The image of the person to be measured, which is photographed by the camera 420, may be adjusted to be consistent with the guide image. When the human body measurement mode is executed, the electronic device 101 analyzes whether the image of the person to be measured is consistent with (or corresponds to) the guide image or not in step 1020. When the image of the person to be measured is not consistent with (i.e., does not correspond to) the guide image, the electronic device 101 does not measure the human body and waits until the photographed image of the person to be measured is consistent with (or corresponds to) the guide image.

The guide image may be an image which guides the user on a posture for measuring the human body of the person to be measured. When the photographed image of the person to be measured is consistent with the guide image, the posture of the person to be measured is sufficient to measure the human body. When the two images are consistent with each other, the electronic device 101 detects this in step 1020 and automatically measures the human body in step 1030. In step 1030, the electronic device 101 receives human body information which is detected by the human body sensor 450, and in step 1040, analyzes the measured human body information. The electronic device 101 starts measuring the human body information (for example, impedance) in step 1030, and automatically captures the appearance of the person to be measured as an image. The measurement of the human body information (for example, impedance) may be finished within about a few seconds to 1 minute.

In step 1040, the electronic device 101 analyzes the measured human body information. The human body information may be body fat information. The electronic device 101 may convert a measurement value of the human body information (for example, impedance) measured in step 1040 into body composition data. The impedance measurement value may be determined according to body water in the human body, and most of the body water may exist in muscles of the human body. In addition, the electronic device 101 may convert the impedance measurement value into body composition data. The electronic device 101 may acquire the body composition data such as body water, protein, minerals, body fat, etc. from the impedance measurement value using a pre-defined conversion equation. The pre-defined conversion equation may use a theoretically determined equation, or may use an equation which is determined by experiments. The electronic device 101 may calculate a body fat percentage using the body composition data acquired by the conversion equation and the height and weight of the person to be measured. In step 1050, the electronic device 101 displays the captured image of the appearance of the person to be measured during the measurement, and the human body information data processed in step 1040 on the display 430. The electronic device 101 may display the captured image of the person to be measured, the height and weight, and the processed body fat percentage on the display 430. The human body information analyzed in the electronic device 101 may be displayed as shown in FIG. 8. The electronic device 101 determines whether the person to be measured wishes to store the human body information or not in step 1060, and when the user wishes to store, stores the human body information in the memory 480 and finishes the measurement.

Figure 11:
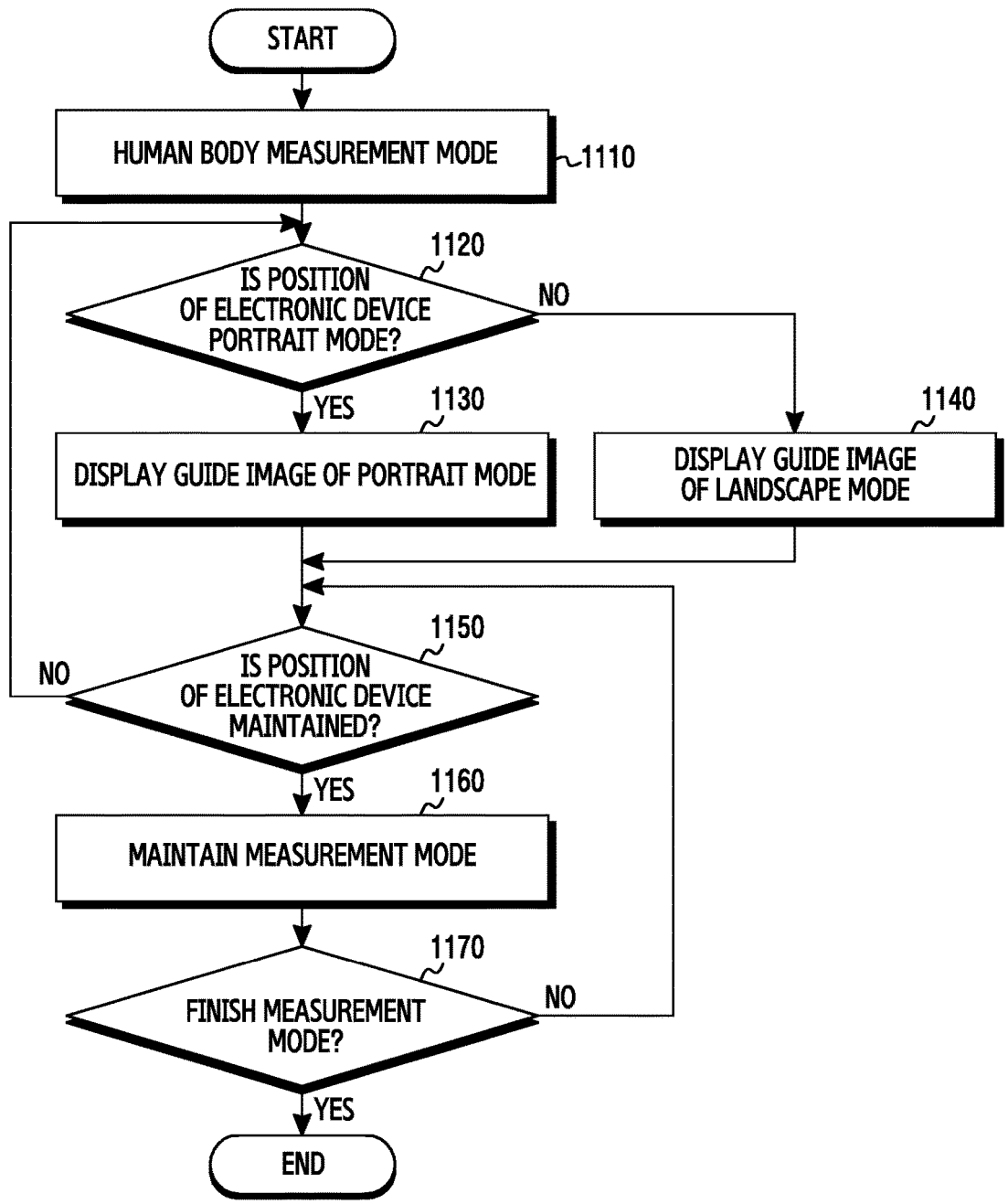
FIG. 11 illustrates a flowchart of a method for displaying a guide image in an electronic device according to various embodiments of the present disclosure.

FIG. 11 illustrates a flowchart of a method for displaying a guide image in an electronic device according to various embodiments of the present disclosure.

Referring to FIGS. 4 and 11, when a human body measurement mode is requested, the electronic device 101 detects this request in step 1110 and performs the human body measurement mode. In this case, the human body measurement mode may be performed not only by a user's measurement mode input, but also by contacting the electrode of the human body sensor 450. The person to be measured may bring a part of his/her body (for example, a finger) into contact with the four electrodes of the human body sensor 450 to measure human body information as shown in FIG. 5B or 5D. The electronic device 101 analyzes the output of the position sensor 460 and detects the position of the electronic device 101 in step 1120. The position of the electronic device 101 may be a landscape display mode or a portrait display mode. The guide image may be a different image in each of the landscape or portrait display mode. For example, the guide image may be the images shown in FIGS. 6B, 6C, and 7B. When the human body measurement mode is executed, the electronic device 101 analyzes the output of the position sensor 460 (for example, an acceleration sensor, a geomagnetic sensor, etc.), and determines a display mode of the electronic device 101.

When the portrait display mode is detected in step 1120, the electronic device 101 displays a guide image of a portrait display mode on the display 430 as shown in FIG. 7B. The guide image of the portrait display mode may be an image which is stored in the memory 480. In addition, the guide image of the portrait display mode may be an image as shown in FIG. 7B, or may be an image of a person to be measured, which was photographed in a previous measurement mode. When the landscape display mode is detected in step 1120, the electronic device 101 displays a guide image of a landscape display mode on the display 430 as shown in FIG. 6B or 6C. The guide image of the landscape display mode may be an image which is stored in the memory 480. In addition, the guide image of the landscape display mode may be an image as shown in FIG. 6B or 6C, or may be an image of a person to be measured which was photographed in a previous measurement mode. As described above, the electronic device 101 may display the guide image and maintain its position. In the case when the position of the electronic device 101 is changed, the measurement posture is changed. When the measurement posture is changed, a measurement error may occur. When the position of the electronic device 101 is changed, the electronic device 101 detects this change in step 1150 and returns to step 1120 to identify the position of the electronic device 101 again and then display a guide image of a corresponding display mode. However, when the same position of the electronic device 101 is maintained, the electronic device 101 executes the measurement mode in step 1160. In this case, the electronic device 101 may perform the human body measurement mode according to the method shown in FIG. 10. In step 1170, the electronic device 101 identifies whether the position of the electronic device 101 is the same until the human body measurement is finished.

A method of operation of an electronic device according to various embodiments of the present disclosure may include, displaying a guide image when a human body measurement mode is detected, acquiring, by a camera, a human body image, displaying the human body image, measuring a human body when the human body image corresponds to the guide image, and outputting a result of the measurement of the human body.

The measuring of the human body may include measuring body fat of the human body corresponding to the human body image. The electronic device may be provided with body fat detection sensors disposed at four electrode points on the electronic device, and when human body contact on the four electrode points is detected, shifting to the human body measurement mode.

Displaying of the guide image may further include identifying a landscape display mode or a portrait display mode of the electronic device. Displaying the guide image may further include displaying the guide image according to the identified display mode.

Measuring the human body may further include capturing the human body image and measuring the body fat based on the guide image and the human body image.

Outputting the result of the measurement of the human body may further include mapping and storing the human body image and the measured body fat. Outputting the result of the measurement of the human body may further include, when an output of the measurement of the body fat is requested, outputting the mapped and stored human body image and body fat.

Displaying the guide image may further include displaying the human body image which was captured in a previous measurement mode as the guide image.

Figure 12:
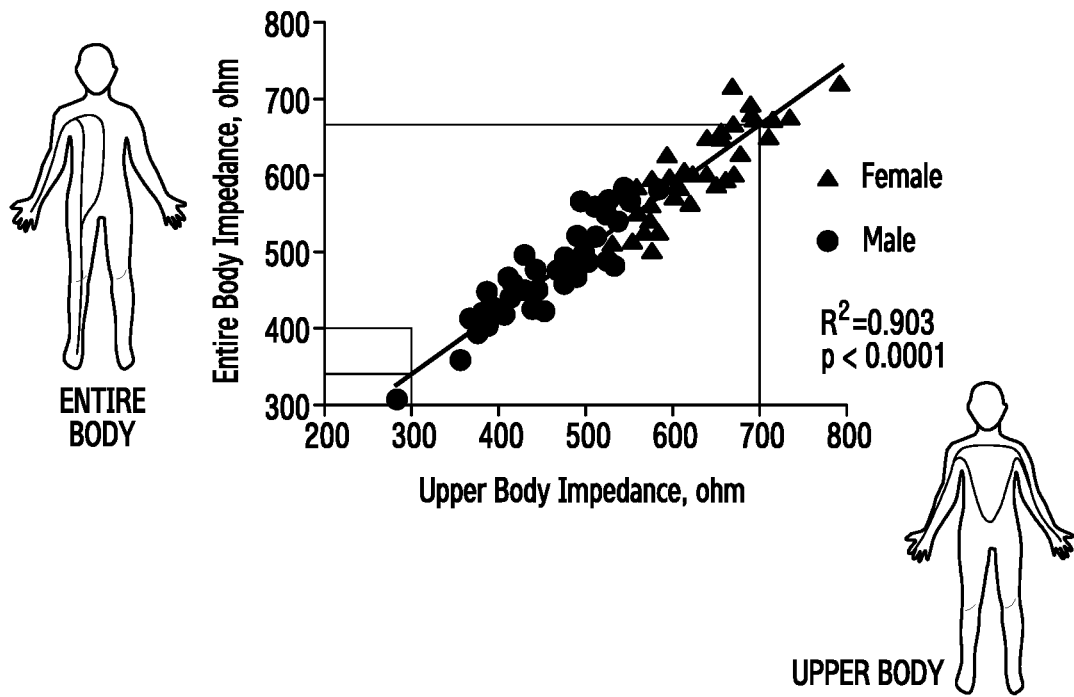
FIG. 12 illustrates an impedance correlation between an entire body 4-electrode and 2-point device and an upper body 4-electrode and 2-point device for measuring body fat according to various embodiments of the present disclosure.

When the body fat is measured, an entire body 4-electrode measuring method and an upper body 4-electrode measuring method may have a similar measurement results. FIG. 12 illustrates an impedance correlation between an entire body 4-electrode and 2-point device and an upper body 4-electrode and 2-point device for measuring body fat according to various embodiments of the present disclosure.

Referring to FIG. 12, as a result of measuring impedance of an experimental group of a plurality of human body subjects, a coefficient of determination of upper body impedance and entire body impedance, $R^2$, is equal to 0.903. Referring to FIG. 4, in the measurement of impedance for measuring body fat, a correlation between the upper body impedance and the entire body impedance is very high. More specifically, when the entire body 4-electrode and 2-point device is replaced with the upper body 4-electrode and 2-point device to measure body fat, the accuracy of measurement of body fat is very high. That is, even when the body fat is calculated by measuring only the upper body impedance with the upper body 4-electrode and 2-point device, which is convenient for a user to carry, the body fat may be calculated with similar accuracy as that when the entire body impedance is measured.

The present disclosure provides a method for measuring human body information in which the user (person to be measured) may measure human body information using a portable electronic device. In addition, the person to be measured maintains a constant posture for measuring human body information according to the guide image displayed on the display, and accordingly, the electronic device enhances the accuracy of measurement of human body information. In addition, the electronic device may display human body information measurement data and the image of the person to be measured on the screen simultaneously in order for the person to be measured to understand his/her health condition and body shape. In addition, the electronic device may form a database by storing measurement data of the person to be measured, a measurement appearance image, measuring date, and manage the database efficiently, thereby helping the person manage their health and body shape.

A computer-readable recording medium may include a program for performing the operations of, when a human body measurement mode is detected, displaying a guide image, acquiring, by a camera, a human body image, displaying the human body image, measuring a human body when the human body image corresponds to the guide image and outputting a result of the measurement of the human body.

While the present disclosure has been shown and described with reference to certain embodiments thereof, it will be understood by those skilled in the art that various changes in form and details may be made therein without departing from the spirit and scope of the disclosure as defined by the appended claims and their equivalents. Therefore, the scope of the present disclosure is defined not by the detailed description of the present disclosure but by the appended claims and their equivalents, and all differences within the scope will be construed as being included in the present disclosure.

What is claimed is:

1. A method of operating an electronic device, the method comprising:
   displaying a guide image which is updated based on a previously acquired human body image;
   acquiring, by a camera, a human body image corresponding to the guide image;
   in response to acquiring the human body image corresponding to the guide image, measuring information regarding the human body by supplying a current to a plurality of electrodes of the electronic device; and
   outputting the information regarding the human body,
   wherein outputting the information regarding the human body comprises:
   mapping and storing the human body image and the information regarding the human body, and
   in response to identifying a request for outputting the information regarding the human body, outputting the stored human body image and the stored information regarding the human body.

2. The method of claim 1, wherein the information regarding the human body comprises at least one of body fat, a muscle mass, body water or minerals.

3. The method of claim 1, wherein the plurality of electrodes of the electronic device comprises four electrodes.

4. The method of claim 1, wherein displaying the guide image comprises:
   determining a display mode of the electronic device, and displaying the guide image based on the determined display mode of the electronic device, and wherein the display mode of the electronic device comprises a landscape display mode and a portrait display mode.

5. The method of claim 1, wherein displaying the guide image comprises displaying the guide image in response to identifying whether the human body contacts the plurality of electrodes of the electronic device.

6. The method of claim 1, further comprising:
determining, based on the human body image, whether to change the guide image, and
if it is determined to change the guide image, updating the guide image based on the human body image.

7. The method of claim 1, wherein measuring the information regarding the human body by supplying the current to the plurality of electrodes of the electronic device comprises:
identifying impedance of the human body by supplying the current to the plurality of electrodes of the electronic device, and
based on the impedance of the human body, measuring the information regarding the human body.

8. An electronic device comprising:
a plurality of electrodes,
a camera,
a display, and
a processor configured to:
control the display to display a guide image which is updated based on a previously acquired human body image;
control the camera to acquire a human body image corresponding to the guide image;
in response to acquiring the human body image corresponding to the guide image, measuring information regarding the human body by supplying a current to the plurality of electrodes of the electronic device; and
output the information regarding the human body,
wherein the processor is further configured to:
output the information regarding the human body by mapping and storing the human body image and the information regarding the human body, and outputting the stored human body image and the stored information regarding the human body in response to identifying a request for outputting the information regarding the human body.

9. The electronic device of claim 8, wherein the information regarding the human body comprises at least one of body fat, a muscle mass, body water or minerals.

10. The electronic device of claim 8, wherein the plurality of electrodes comprises four electrodes which are mounted on a plurality of side surfaces of the electronic device.

11. The electronic device of claim 8, wherein the plurality of electrodes comprises four electrodes which have two electrodes mounted on a plurality of side surfaces of the electronic device, and two electrodes mounted on a rear surface of the electronic device.

12. The electronic device of claim 8, wherein, the processor is configured to display the guide image in response to identifying whether the human body contacts the plurality of electrodes of the electronic device.

13. The electronic device of claim 8, wherein the electronic device further comprises a position sensor configured to identify a position of the electronic device, and
the processor is further configured to:
determine, based on the position of the electronic device, a display mode of the electronic device, and
display the guide image based on the determined display mode of the electronic device,
wherein the display mode of the electronic device comprises a landscape display mode and a portrait display mode.

14. The electronic device of claim 8, wherein the processor is further configured to:
determine, based on the human body image whether to change the guide image,
if it is determined to change the guide image, update the guide image based on the human body image.

15. The electronic device of claim 8, wherein the processor is configured to:
identify impedance of the human body by supplying the current to the plurality of electrodes of the electronic device, and
based on the impedance of the human body, measure the information regarding the human body.

16. A non-transitory computer readable recording medium comprising a program for executing the operations of:
displaying a guide image which is updated based on a previously acquired human body image;
acquiring, by a camera, a human body image corresponding to the guide image;
in response to acquiring the human body image corresponding to the guide image, measuring information regarding the human body by supplying a current to a plurality of electrodes of the electronic device; and
outputting the information regarding the human body,
wherein outputting the information regarding the human body comprises:
mapping and storing the human body image and the information regarding the human body, and
in response to identifying a request for outputting the information regarding the human body, outputting the stored human body image and the stored information regarding the human body.

* * * * *